United States Patent [19]
Knifton et al.

[11] Patent Number: 5,457,243
[45] Date of Patent: Oct. 10, 1995

[54] NEUTRALIZATION OF CRUDE MTBE EFFLUENT STREAMS USING SOLID BASES

[75] Inventors: John F. Knifton; Mark A. Mueller, both of Austin, Tex.; Michael W. Peters, Gilbert, Ariz.

[73] Assignee: Texaco Chemical Inc., White Plains, N.Y.

[21] Appl. No.: 172,345

[22] Filed: Dec. 23, 1993

[51] Int. Cl.⁶ .................................................. C07C 41/00
[52] U.S. Cl. ........................................... 568/697; 568/699
[58] Field of Search ....................................... 568/697, 699

[56] References Cited

U.S. PATENT DOCUMENTS

| | | | |
|---|---|---|---|
| 4,182,913 | 1/1980 | Takezono et al. | 568/697 |
| 4,404,409 | 9/1983 | Fujiwara et al. | 568/697 |
| 5,260,493 | 11/1993 | Harandi et al. | 568/697 |

OTHER PUBLICATIONS

McKenzie et al, J of Catalysis, 138 pp. 547–549, 560 (1992).

*Primary Examiner*—Johann Richter
*Assistant Examiner*—Kimberly J. Kestler
*Attorney, Agent, or Firm*—James L. Bailey; Kenneth R. Priem; Cynthia L. Hunter

[57] ABSTRACT

Disclosed is a method for removing organic acids and derivatives thereof from a crude methyl tertiary butyl ether (MTBE) stream of the type found in the feed to, or effluent from, a reactor for a one-step process for producing MTBE which comprises:

contacting said crude MTBE stream in a treating zone over one or more beds of a solid base for a period of time sufficient to neutralize said organic acids and derivatives thereof; and withdrawing a substantially organic acid-free crude MTBE product from said treating zone.

12 Claims, 1 Drawing Sheet

NEUTRALIZATION OF CRUDE MTBE EFFLUENT STREAMS USING SOLID BASES

FIELD OF THE INVENTION

This invention relates to the neutralization of crude methyl tertiary butyl ether (MTBE) streams, including, for example the feed to, or effluent from, a one-step process for producing methyl tertiary butyl ether. More particularly, this invention relates to a method for neutralizing organic acids and esters in crude MTBE streams, such as, for example, the neutralization of formic acid and hydrolyzable formic esters, particularly methyl formate and butyl formate. Still more particularly, this invention relates to the neutralization of the crude MTBE streams using a series of different classes of solid bases.

BACKGROUND OF THE INVENTION

It is well-known that acids are formed during the oxidation of hydrocarbons such as isobutane, by the decomposition of peroxides such as t-butylhydroperoxide in crude tertiary butyl alcohol (tBA) feed, and from the hydrolysis of formates present in the tBA feed, resulting in the presence of acids such as, for example, formic acid, acetic acid, and isobutyric acid in the feed to a one-step process for making MTBE. In MTBE pilot plants where carbon steel is sometimes used in the one-step reactor and distillation towers, these acids have been shown to cause significant corrosion if left untreated.

One solution to this problem is sodium hydroxide injection into the effluent stream of the MTBE one-step reactor in order to neutralize said acids, however this solution may lead to unacceptable corrosion rates certain points in the process. In addition, the injection of caustic poses other concerns such as potential foaming in downstream distillation columns, formation of a second liquid phase with the additional water introduced with the caustic, and the necessity to control pH, which is notoriously difficult.

U.S. Pat. No. 5,106,458 discloses a process for removing methyl formate from impure propylene oxide which comprises contacting said impure propylene oxide in a treating zone with a strongly basic ion exchange resin for a period of time sufficient to convert said methyl formate to formic acid and methanol. The preferred basic ion exchange resin is a styrene divinylbenzene copolymer containing quaternary ammonium groups.

One reference in the art which addresses the topics of adsorption and ion exchange is Perry, R. H. and Green, D. W., *Perry's Chemical Engineer's Handbook*, 6th Ed., Sec. 16, McGraw-Hill, 1984. This text includes an analysis of design strategies for various fixed-bed separations.

Another reference recognized in the art is Schweitzer, P. A., *Handbook of Separation Techniques for Chemical Engineers*, p. 387, McGraw-Hill, 1979. Section 1.12, by Robert Anderson, includes a very good overview of the factors involved in a resin system.

From a survey of references available in the art, it would appear that the accepted method of attempting to remove formic acid and other organic acids from the effluent of a one-step process for producing MTBE is the previously mentioned injection of sodium hydroxide into the stream, however, it is apparent that method can cause problems downstream, as well as other disadvantages.

It would represent a distinct advance in the art if there were a method available for treating MTBE effluent streams which did not contribute to corrosion. It would represent an advance over any method known presently in the art if the formic acid, methyl formate and butyl formate could be removed from an MTBE effluent stream in a manner which did not contribute to problems such as foaming in downstream distillation columns, formation of a second liquid phase with the addition of water introduced with the caustic, and the necessity to control pH.

SUMMARY OF THE INVENTION

In accordance with the foregoing, there is disclosed a method for neutralizing organic acids and esters in the feed, or effluent, of a one-step process for synthesizing MTBE which comprises continuously passing the MTBE feed or effluent over one or more beds of a solid base selected from the classes consisting of:

1) Hydrotalcites;
2) Alkali metal-treated hydrotalcites;
3) Amine functionalized polysiloxanes;
4) Alkali metal or alkaline earth metal-exchanged zeolites;
5) Alkali metal-treated Group II, III or IV oxides;
6) Magnesium silicates; and
7) Weakly basic ion exchange resins.

The use of the method of this invention alone, or in combination with the injection of caustic, for removing organic acids and esters in the feed or effluent of a one step process for making MTBE will significantly address the problem of the corrosion of carbon steel, assist in controlling pH and reduce or eliminate possible operating problems such as foaming.

One particular improvement over the art is that the resin bed, or solid inorganic base, can also be placed in the tertiary butyl alcohol feed to the MTBE plant (optionally prior to peroxide decomposition) and thus prior to the one step reactors, as well as in the MTBE effluent. This particular option would allow the MTBE reactors to be constructed of carbon steel and would also avoid poisoning of the etherification catalyst.

DESCRIPTION OF THE PREFERRED EMBODIMENT

Figure 1:
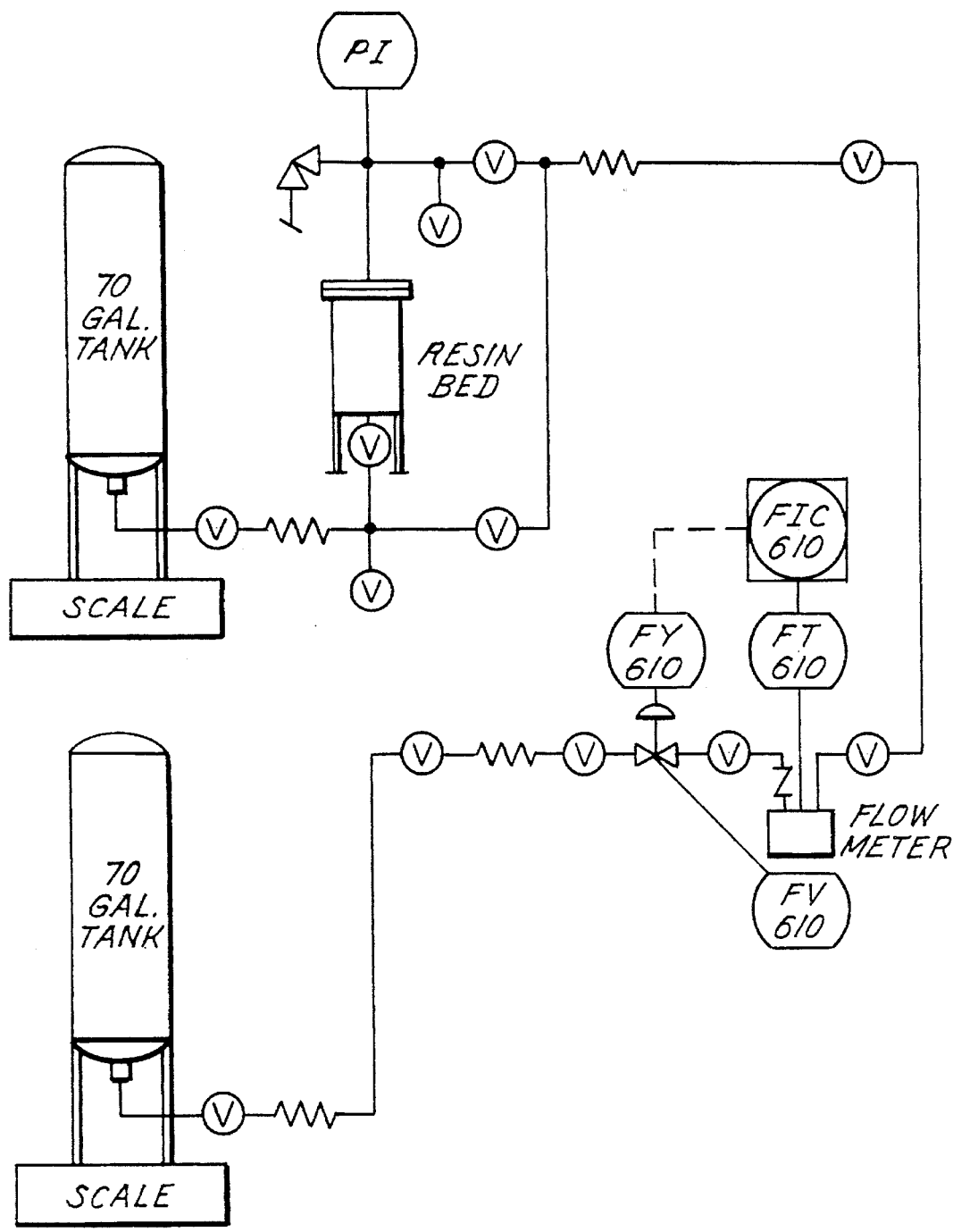
FIG. 1 is a schematic drawing of the equipment layout used in Examples VII and VIII.

The crude methyl tertiary butyl ether(MTBE) to be treated in the instant invention also contains isobutylene($C_4H_8$), methanol(MeOH) and t-butanol(tBA) and has a pH of about 4–5, in most instances about 4.3 to 4.8. It is desirable to neutralize said crude MTBE stream so that the pH after treatment is as close as possible to 7, or neutral, in order to avoid the problems mentioned above. The current method of neutralizing is to inject caustic to remove the organic acids.

In the method of this invention the acid content of the effluent is close to quantitatively removed. In Examples I through VI the effectiveness of these methods for removing formic acid, acetic acid, isobutyric acid, etc. was measured by the pH of the effluent, after contact with the designated base. The treated effluent pH was, in the majority of cases, 7.0±.50.

In the instant invention there is disclosed a method of neutralization of crude MTBE effluent streams using solid bases from the group consisting of hydrotalcites, alkali metal-treated hydrotalcites, magnesium silicates, alkali metal and alkaline earth metal-exchanged zeolites, amine-functionalized polysiloxanes, and alkali and alkaline earth-treated Group II, III or IV oxides.

Hydrotalcites are a group of magnesium, aluminum hydroxy carbonates. The hydrotalcite may be a naturally occurring anionic clay, or a synthetic hydrotalcite, or a mixture of both. The general formula for the hydrotalcite clay is:

$$Mg_6Al_2(OH)_{16}CO_3 \cdot 4H_2O$$

The structure of hydrotalcite is similar to brucite, $Mg(OH)_2$, where $Mg^{2+}$ is octahedrally coordinated to the surrounding hydroxide ions. These magnesium hydroxide octahedral share adjacent edges to form sheets or layers. In hydrotalcite, some of the magnesium is isomorphously replaced by $Al^{3+}$ and the atomic ratio of magnesium to aluminum can be quite variable. However, values between 1.7 and 4.0 are usually reported for Mg:Al atomic ratios in synthetic samples. Substitution of $A^{3+}$ for $Mg^{2+}$ produces net positive charges on the metal hydroxide layers because the $Al^{3+}$ remains octahedrally coordinated to the hydroxyl groups. This layer charge in naturally occurring hydrotalcite is balanced by interlayer carbonate (see: A. L. McKenzie et al., J. Catal., 138, 547 (1992)). In addition to anions, water molecules are also located between the metal hydroxide layers.

The changes that occur during thermal calcination include, with increasing temperature, first loss of interlayer water, followed by dehydroxylation and decomposition of interlayer carbonate to $CO_2$. Removal of $CO_2$ and structural water from calcined hydrotalcite is accompanied by an increase in surface area, ultimately yielding mixed oxides of 200–300 $m^2/g$.

Calcined hydrotalcites are potentially useful as base catalysts and catalytic supports since the high surface area is stable to steam treatment (see: ibid., p. 548).

A commercially available hydrotalcite which is useful is KW-2000. KW-2000 is a calcined hydrotalcite, manufactured by Kyowa Chemical Industry Co., Ltd. of Japan.

The second group of solid bases comprises hydrotalcites treated with a Group IA, alkali metal selected from the group consisting of lithium, sodium, potassium, rubidium or cesium. Preferred alkali metals are potassium and sodium. The amount of alkali metal on the hydrotalcite should range from about 0.1% to 30% by weight of the total catalyst.

An alkali metal-treated hydrotalcite which is particularly effective is a sodium-treated KW-2000 hydrotalcite identified as Na/KW-2000.

Another suitable solid base is magnesium silicate having the general composition $3MgSiO_3 \cdot 5H_2O$ and normally derived from the interaction of a magnesium salt and a soluble silicate. A synthetic adsorptive magnesium silicate is "Magnesol®", available from the Dallas Group of America.

A fourth class of suitable bases is amine functionalized polysiloxanes(ethylenediamino functionalized polysiloxane). Polysiloxanes are products available by hydrolysis of dialkyldichlorosilanes with water followed by treatment with polyalcohols, as well as the products available by addition of polysiloxane dihydrides to olefins, such as alkyl alcohol or acrylic acid, as described in U.S. Pat. No. 4,920,173, incorporated herein by reference.

Polysiloxanes have the structure:

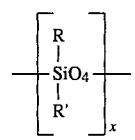

where R and R' are the same or different alkyl or aryl groups having from 1 to 6 carbon atoms, and x is an integer of at least 20.

Polysiloxanes usually have a molecular weight of from 500 to 200,000 and a kinematic viscosity of from 50 to $2\times10^6$ $mm^2$ $sec.^{-1}$. Preferably the polysiloxanes have a kinematic viscosity from $5\times10^2$ to $5\times10^4$ $mm^2$ $sec.^{-1}$, most preferably $3\times10^3$ to $3\times10^4$ $mm^2$ $sec.^{-1}$ groups. The polysiloxanes are generally blocked with trimethylbutyl groups, but other end blocking groups are available as discussed in U.S. Pat. No. 4,818,292.

U.S. Pat. No. 4,704,425 describes suitable agents for complexing with polysiloxanes, such as, for example, ethylene diamine tetraacetic acid (EDTA), sodium nitrilotriacetate (NTA) and sodium diethylene triaminopentaacetate (DTPA). A suitable commercially available ethylenediamine functionalized polysiloxane is Deloxan DAP, manufactured by DeGussa Corporation and available in spherical form.

The fifth class includes zeolites exchanged with metals selected from alkali metals and alkaline earth metals. Suitable zeolites are preferably Y-zeolites. The preferred catalysts for use in the dealuminated form are certain crystalline aluminosilicate zeolites, particularly the isostructural group of faujasite zeolites that include the synthetic X- and Y-zeolites. The preferred zeolites for dealumination are the Y-zeolites.

The unit cells of faujasite zeolites are cubic, $a_o$~2.5 nm, and each contains 192 silicon- or aluminum-centered oxygen tetrahedra which are linked through shared oxygen atoms. Because of the net negative charge on each of the aluminum-centered tetrahedra, each unit cell contains an equivalent number of charge-balancing cations. These are exclusively sodium ions in zeolites in their synthesized form. Typical cell contents for the Y-zeolites in the hydrated form are:

$$Na_{56}[(AlO_2)_{56}(SiO_2)_{136}]_x \cdot 250H_2O$$

Y-zeolites are distinguished on the basis of the relative concentration of silicon and aluminum atoms and the consequent effects on detailed structure and related chemical and physical properties. The aluminum atoms in the unit cell of Y-zeolite vary from 76 to 48, resulting in a Si:Al ratio between 1.5 and 3.0. Both the cation concentration and charge density on the aluminosilicate structure are lower for Y-zeolites than for X-zeolites, where the aluminum atoms in the unit cell vary from 96 to 77.

The feature which determines the difference between faujasites and other zeolites built up from sodalite units is the double 6-membered ring or hexagonal prism, by which the units are linked. The sodalite unit, or β-cage, can be represented by a truncated octahedron, with the 24 silicon or aluminum atoms(designated T atoms) taking positions at the vertices. The 36 oxygen atoms are displaced from the midpoints of the edges joining the vertices in order to attain tetrahedral configuration around the T atoms. The free diameter of the void within the β-cage is 0.66 nm, but only the smallest molecules can enter through the 0.22 nm diameter opening in the distorted ring of six oxygen atoms associated with each hexagonal face. Each sodalite unit is linked tetrahedrally across hexagonal faces by six bridging oxygens to four other sodalite units. The larger void spaces enclosed by sodalite units and hexagonal prisms are termed α-cages, or supercages. The α-cage is a 26-hedron with a free diameter of ~1.3 nm, and it can be entered through four distorted 12-member rings of diameter 0.80–0.90 nm. In this way each α-cage is tetrahedrally joined to four others giving a complex system of void space extending throughout the zeolite structure. The α- and β-cages together give Y-zeolites, along with X-zeolites, the largest void volume of any known zeolites, which is ca. 50 vol % of the dehydrated crystal. From the catalytic viewpoint, the α-cages are by far the most important, since, unlike the β-cages, they permit entry of numerous aliphatic and aromatic compounds.

These Y-zeolites are particularly effective in the dealuminated form. Preferably, said Y-zeolites are dealuminated by ammonium exchange followed by calcination, or by treatment with ethylenediaminetetraacetic acid (EDTA) or other chelating agents, or by treatment with fluorine or a fluorine-containing compound such as silicon tetrafluoride or ammonium fluorosilicate, or hydrothermal treatment and/or acid treatment. Said dealuminated Y-zeolites should have a silica-to-alumina molar ratio of greater than three, preferably a ratio of 5 or greater and most preferably a silica-to-alumina ratio of 5 to 100. The examples demonstrate the usefulness of catalysts having a silica-to-alumina ratio of 5 to 100.

Examples of suitable commercially available dealuminized Y-zeolites include UOP's LZY-82 and LZY-72, PQ corporation's CP-304-37 and CP-316-26, UOP's Y-85, Y-84, LZ-10, LZ-210, and CP316-66, also from PQ corporation.

In a preferred embodiment the dealuminated Y-zeolite is modified with an alkali metal, such as, for example cesium in an amount of about 0.1% to 30% by weight. A commercially available Y-zeolite having a silica:alumina ratio of about five and having about 10% by weight Cs deposited thereon is CP316-66.

The unit cell size and $SiO_2/Al_2O_3$ molar ratio for typical dealuminated Y-zeolites are noted in the following table:

| ZEOLITE TYPE | UNIT CELL SIZE, A | $SiO_2/Al_2O_3$ MOLAR |
| --- | --- | --- |
| LZY-82 | 24.53 | 7.8 |
| LZY-85 | 24.49 | 9.1 |
| LZY-10 | 24.32 | 23.7 |
| LZY-20 | 24.35 | 18.9 |
| LZY-84 | 24.51 | 8.4 |
| LZ-210 | 24.47 | 9.9 |
| LZY-72 | 24.52 | 8.1 |
| CP316-26 | 24.26 | 45.7 |

The sixth class of bases for neutralizing crude MTBE streams includes oxides of Group II, III or IV of the Periodic Table treated with metals from Group IA or IIA, alkali or alkaline earth metals. Preferred oxides are alumina and silica.

The preferred oxide supports in the instant invention comprise theta-alumina (θ-alumina). The θ-alumina support is produced by calcination of a γ-alumina support for 1 to 4 hours at a temperature from about 800° to 1200° C., thereby increasing pore size. A preferred temperature is about 1050° C. Thereafter the θ-alumina support is impregnated with metal salt solution. The use of θ-alumina is demonstrated in Example VI.

Suitable θ-aluminas are those which satisfy the following X-ray diffraction pattern:

| d ($10^{-10}$ m) | I/Io |
| --- | --- |
| 1.39 | 100 |
| 2.85 | 75–85 |
| 2.72 | 60–80 |
| 2.43 | 70 |
| 2.01 | 45–80 | having a surface area between 50 and 200 m²/g and being substantially free of pores with a diameter less than 4.0 nm. The alumina has a pore size distribution substantially between 3.5 and 30 nm, rather than between 3.5 and 120 nm as measured by nitrogen desorption.

Example VI demonstrates the use of theta alumina treated with cesium.

The last class of bases which are effective is a group of weakly basic anionic polymeric catalysts having an organic polymer backbone, e.g., a styrene-divinylbenzene polymer structure, and an amine-containing a functional structure selected from: —N(CH$_3$)$_2$, —NRH or —NR$_2$, bonded to said polymer backbone, where R is an alkyl group having 2 to 20 carbon atoms. Examples include AMBERLYST® A-21, A-22 or A-23 available from Rohm and Haas. Particularly effective is Amberlyst® A-21, having the dimethylamine functionality, described in "Technical Bulletin Fluid Process Chemicals—Amberlyst A-21", incorporated herein by reference in its entirety, available from Rohm and Haas, Philadelphia, Pa. 19105.

The method used in Examples I through VI was to charge the various solid bases to an upflow, continuous reactor. Then a mixture of crude MTBE, also containing isobutylene, methanol and t-butanol and having a pH of about 4.3→4.8 was pumped upflow through the reactor bed at 25° C., under 100 psi back pressure, for a period of 80 hours or more. The liquid feed rate was 50 cc/hr. In Example VII, the MTBE effluent feed stream pH was slightly more acidic (pH 3.7→3.8).

A feature of the instant invention which constitutes a great improvement over anything available in the art is that the catalyst beds can also be placed in the tBA feed to the MTBE plant, prior to the one-step reactors. This would allow those reactors to be constructed of carbon steel, resulting in significant cost savings. Since caustic, currently used, remains in solution, it cannot be injected at any point prior to the one-step reactor, because that would poison the acid catalyst contained in the one-step reactor.

The use of a weakly basic anionic polymer to remove acids from the MTBE feed, compared with the MTBE effluent, is demonstrated in Example VIII, where the acidity was reduced 92% and the pH brought much closer to neutral. Neutralization of similar MTBE feed is demonstrated in Examples IX and X using KW-2000 and magnesol.

Generally, said neutralization of MTBE effluent or feed with the solid bases described supra may be conducted at temperatures from ambient to 200° C. or more, but preferably in the range from ambient to 150° C. The operating pressure is normally sufficient to maintain the liquid feeds and effluents in the liquid phase and is typically zero to 1000 psi, but preferably ca. 100 psi. The liquid feed rates in continuous processing are generally in the range 0.1 to 10 LHSV.

The following examples are given to demonstrate the method of the invention. It is understood that the examples are given only for illustration and that the invention is not intended to be limited thereby.

EXAMPLE I

This example illustrates the neutralization of crude MTBE stream using a hydrotalcite.

To a 50 cc capacity, upflow, continuous reactor was charged 50 cc of hydrotalcite powder (KW-2000, from Kyowa Chemical Co.). A mixture of crude methyl t-butyl ether effluent, also containing isobutylene ($C_4H_8$), methanol (MeOH) and t-butanol (tBA), having a pH of 4.32 and a titratable acidity of 0.57 mg KOH/g, was pumped upflow through the reactor bed at 25° C., under 100 psi back pressure, for a period of 80 hour during which time samples of reactor effluent were withdrawn and analyzed. The liquid feed pump rate was 50 cc/hr.

All reactor effluent samples were found to be close to pH neutral (pH>6.5) and showed no significant changes in organic composition as determined by glc.

Typical analyses data are summarized in Table I.

EXAMPLES II→VI

These examples illustrate the neutralization of crude MTBE streams using a variety of solid bases.

Following the procedures of Example I and using the same acidic MTBE crude effluent, neutralization of said effluent was demonstrated in varying degrees using:

a) Sodium-treated hydrotalcite—see Table II.

b) Magnesol reagent—see Table III.

c) Cesium exchanged Na-Y-zeolite—see Table IV.

d) Ethylenediamino-functionalized polysiloxane—see Table V.

e) Cesium-treated θ-alumina—see Table VI.

Superior performances were realized with the alkali metal-treated hydrotalcite and with the magnesium silicate, magnesol reagent (Examples II and III).

TABLE I

MTBE NEUTRALIZATION

| Ex. | Catalyst | Time on Stream (Hrs) | Sample | pH | Acidity (mg KOH/g) | $C_4H_8$ | MeOH | tBA | MTBE |
|---|---|---|---|---|---|---|---|---|---|
| I | KW-2000[a,b] |  | FS-1 | 4.32 | 0.57 | 1.0 | 40.0 | 21.8 | 35.6 |
|  |  | 4 | 1 | 7.65 | 0.00 | 0.8 | 40.0 | 22.9 | 35.1 |
|  |  | 15 | 2 | 7.45 | 0.034 | 0.5 | 41.3 | 24.4 | 32.5 |
|  |  | 22 | 3 | 6.78 | 0.027 | 0.6 | 41.0 | 23.3 | 33.9 |
|  |  | 39 | 4 | 6.57 | 0.038 | 1.2 | 39.8 | 22.1 | 35.6 |
|  |  | 46 | 5 | 6.80 | 0.080 | 2.0 | 38.3 | 20.3 | 37.3 |
|  |  | 110 | 6 | 7.23 | 0.061 | 1.8 | 39.3 | 21.6 | 36.0 |

[a]From Kyowa Chemical Co., powder
[b]Operating conditions: 25° C., 100 psi, LHSV 1

TABLE II

MTBE NEUTRALIZATION

| Ex. | Catalyst | Time on Stream (Hrs) | Sample | pH | Acidity (mg KOH/g) | $C_4H_8$ | MeOH | tBA | MTBE |
|---|---|---|---|---|---|---|---|---|---|
| II | 6798-55[a] |  | FS-2 | 4.82 | 0.49 | 1.8 | 37.8 | 16.6 | 42.2 |
|  |  | 17 | 2 |  |  | 1.6 | 38.4 | 17.0 | 41.4 |
|  |  | 23 | 3 | 7.01 | 0.01 | 1.8 | 38.4 | 17.1 | 41.2 |
|  |  | 41 | 4 | 7.61 | 0.02 | 1.8 | 38.2 | 16.8 | 41.6 |
|  |  | 48 | 5 | 7.15 | 0.02 | 1.7 | 38.1 | 16.8 | 41.8 |
|  |  | 66 | 6 | 7.0 | 0.07 | 1.0 | 39.0 | 17.4 | 41.2 |
|  |  | 71 | 7 | 7.32 | 0.06 | 1.6 | 38.5 | 17.1 | 41.2 |
|  |  | 80 | 8 | 6.83 | 0.03 | 1.5 | 38.6 | 17.1 | 41.2 |

[a]Na on KW-2000, Na, 5.9%, powder

TABLE III

MTBE NEUTRALIZATION

| Ex. | Catalyst | Time on Stream (Hrs) | Sample | pH | Acidity (mg KOH/g) | $C_4H_8$ | MeOH | tBA | MTBE |
|---|---|---|---|---|---|---|---|---|---|
| III | Magnesol[a] |  | FS-1 | 4.82 | 0.49 | 1.8 | 37.6 | 16.5 | 42.5 |
|  |  | 4 | 1 | 7.25 | 0.02 | 1.7 | 37.2 | 16.3 | 43.2 |
|  |  | 22 | 2 | 7.05 | 0.03 | 1.8 | 37.7 | 16.6 | 42.3 |
|  |  | 28 | 3 | 7.13 | 0.04 | 1.8 | 37.6 | 16.5 | 42.5 |
|  |  | 47 | 4 | 6.94 | 0.08 | 1.7 | 38.0 | 17.1 | 41.7 |
|  |  | 52 | 5 | 6.98 | 0.06 | 1.7 | 38.4 | 16.9 | 41.5 |
|  |  | 70 | 6 | 6.71 | 0.09 | 1.5 | 37.8 | 16.7 | 42.5 |

TABLE III-continued

MTBE NEUTRALIZATION

| Ex. | Catalyst | Time on Stream (Hrs) | Sample | pH | Acidity (mg KOH/g) | Comp. (%) $C_4H_8$ | MeOH | tBA | MTBE |
|---|---|---|---|---|---|---|---|---|---|
| | | 79 | 7 | 6.74 | 0.07 | 1.7 | 38.1 | 17.0 | 41.8 |

[a]From the Dallas Group, powder

TABLE IV

MTBE NEUTRALIZATION

| Ex. | Catalyst | Time on Stream (Hrs) | Sample | pH | Acidity (mg KOH/g) | Comp. (%) $C_4H_8$ | MeOH | tBA | MTBE |
|---|---|---|---|---|---|---|---|---|---|
| IV | 052-93-6895-136[a] | | FS-1 | 4.8 | 0.60 | 1.6 | 37.7 | 16.5 | 42.8 |
| | | 7 | 1 | 7.4 | 0.02 | 1.6 | 38.3 | 17.1 | 41.5 |
| | | 24 | 2 | 7.3 | 0.03 | 1.7 | 37.5 | 16.6 | 42.5 |
| | | 29 | 3 | 7.3 | 0.03 | 1.8 | 37.6 | 16.7 | 42.4 |
| | | 47 | 4 | 6.0 | 0.15 | 1.7 | 37.9 | 16.7 | 42.2 |
| | | 55 | 5 | 5.7 | 0.23 | 1.4 | 38.0 | 16.7 | 42.4 |
| | | 71 | 6 | 5.3 | 0.36 | 1.8 | 37.3 | 16.5 | 42.8 |
| | | 79 | 7 | 5.2 | 0.40 | 1.7 | 37.4 | 16.6 | 42.6 |

[a]10% cs on NaY, CP316-66, 1/16" extrudates

TABLE V

MTBE NEUTRALIZATION

| Ex. | Catalyst | Time on Stream (Hrs) | Sample | pH | Acidity (mg KOH/g) | Comp. (%) $C_4H_8$ | MeOH | tBA | MTBE |
|---|---|---|---|---|---|---|---|---|---|
| V | Deloxan DAP[a] | | FS-1 | 4.32 | 0.57 | 1.0 | 40.0 | 21.8 | 35.6 |
| | | 15 | 1 | 6.42 | 0.11 | 1.7 | 39.6 | 21.8 | 35.7 |
| | | 39 | 2 | 4.28 | 0.54 | 1.7 | 39.6 | 23.0 | 34.5 |
| | | 45 | 3 | 4.26 | 0.55 | 1.3 | 39.9 | 22.2 | 35.0 |
| | | 65 | 4 | 4.24 | 0.58 | 1.4 | 40.0 | 22.6 | 34.5 |
| | | 71 | 5 | 4.18 | 0.64 | 1.4 | 39.9 | 22.6 | 34.6 |
| | | 89 | 6 | 4.18 | 0.55 | 1.4 | 39.9 | 22.6 | 34.4 |

[a]Ethylenediamino functionalized polysiloxane, 0.2–0.3 mm spheres

TABLE VI

MTBE NEUTRALIZATION

| Ex. | Catalyst | Time on Stream (Hrs) | Sample | pH | Acidity (mg KOH/g) | Comp. (%) $C_4H_8$ | MeOH | tBA | MTBE |
|---|---|---|---|---|---|---|---|---|---|
| VI | 6798-34R$_2$[a] | | FS-1 | 4.8 | 0.55 | 1.3 | 37.8 | 16.7 | 42.6 |
| | | 6 | 1 | 7.8 | 0.02 | 1.1 | 38.6 | 17.6 | 41.2 |
| | | 25 | 2 | 7.6 | 0.05 | 1.4 | 37.7 | 16.4 | 42.9 |
| | | 30 | 3 | 6.7 | 0.07 | 0.9 | 38.6 | 17.3 | 41.8 |
| | | 48 | 4 | 5.0 | 0.43 | 1.2 | 38.5 | 17.2 | 41.6 |
| | | 52 | 5 | 5.0 | 0.45 | 1.1 | 38.3 | 17.0 | 42.0 |
| | | 59 | 6 | 5.0 | 0.43 | 1.3 | 37.6 | 16.3 | 43.2 |
| | | 82 | 7 | 4.9 | 0.47 | 1.3 | 38.5 | 17.0 | 41.7 |

[a]Cesium on θ-Alumina, 1/32" extrudates

EXAMPLE VII

MTBE one-step reactor effluent material produced in a MTBE pilot plant reactor was passed over a resin bed containing 2000 ml of Amberlyst® A-21 basic anion exchange resin for a period of 80 hours. A sketch of the equipment layout is shown in FIG. 1. The flow rate of the effluent material was such that a space velocity through the bed of 1 cc/cc/hr was maintained. The resin bed was operated at ambient temperature and at a pressure of 80 psig. Samples were taken of the material before and after the resin bed. The approximate feed composition and the pH and acid number of the material before and after the resin bed are shown below.

TABLE VII

Feed Composition for Example VII.

|  | Weight Percent |
| --- | --- |
| Water | 11.2 |
| Isobutylene | 2.8 |
| Methanol | 30.5 |
| Acetone | 1.1 |
| Isopropyl alcohol | 1.2 |
| Tert-butyl alcohol | 12.5 |
| MTBE | 40.7 |

TABLE VIII

Results for Example VII.

| Inlet | | Outlet | |
| --- | --- | --- | --- |
| pH | Acid No. (mg KOH/g) | pH | Acid No. (mg KOH/g) |
| 3.68[1] | 1.05 | 6.01[2] | 0.20 |
| 3.80[1] | 0.66 |  | 0.11 |
|  | 0.69 |  | 0.15 |

[1]Inlet pH taken from previous typical analyses of one-step reactor effluent material, not from specific effluent material used for resin bed study.
[2]Outlet pH taken from drum containing material accumulated during resin bed study.

As can be seen from Table VIII, the resin bed reduced the acid content of the feed material by an average of 81% (basis mg KOH/g, acid No.) in addition to increasing the pH much closer to a neutral value of 7.0.

EXAMPLE VIII

Example VII was given to show the effectiveness of the resin bed in one of the two most likely locations for the bed, that being in the effluent of the MTBE one-step reactor. The second likely location for a resin bed would be in the tBA feed to the MTBE plant. To illustrate the effectiveness of the resin bed in this location, an experiment virtually identical to that described in Example VII was performed with the main difference being that crude tBA feed produced in the PO pilot plant was passed through the bed, instead of one-step reactor effluent. The equipment layout and operating conditions were identical. The same charge of Amberlyst® A-21 catalyst was used after it was washed with deionized water and regenerated with a 4% sodium hydroxide solution. The tables below show the composition of the feed to the bed and the results of analyses taken of the inlet and outlet streams.

TABLE IX

Feed Composition for Example VIII.

|  | Weight Percent |
| --- | --- |
| Water | 0.2 |
| Methanol | 0.1 |
| Acetone | 0.8 |
| Isopropyl Alcohol | 0.2 |
| Tert-butyl Alcohol | 98.7 |

TABLE X

Results of Example VIII.

| Inlet | | Outlet | |
| --- | --- | --- | --- |
| pH | Acid No. (mg KOH/g) | pH | Acid No. (mg KOH/g) |
| 4.28 | 0.67 | 5.80 | 0.04 |
| 4.04 | 0.59 | 6.90 | 0.06 |

As in Example VII, the acid content of the feed is dramatically reduced and the pH brought much closer to neutral. In this case, the acid was reduced an average of 92% (basis acid No. measured by titration as mg KOH/g).

EXAMPLES IX AND X

These examples illustrate the neutralization of crude MTBE feedstock, rich in t-butanol (tBA) plus methanol, using the solid inorganic bases.

Following the procedures of Example 1, a crude t-butanol/methanol feedstock similar to that described in Example VIII was fed to said 50 cc capacity reactor, filled with solid inorganic base, at 120° C. and LHSV of 0.25, under 300 psi of pressure for a period of ca. 86 hours. Neutralization of said MTBE feed was demonstrated using:

a) Hydrotalcite (KW-2000)—see Table XI
b) Magnesium silicate (magnesol reagent)—see Table XII
Superior performing was achieved with the hydrotalcite.

TABLE XI

| | | | | tBA/MeOH Neutralization | | | | | | |
| --- | --- | --- | --- | --- | --- | --- | --- | --- | --- | --- |
| Ex. | Base | Temp. (°C.) | LHSV | Time on Stream (Hrs) | Sample | pH | Acidity (mg KOH/g) | $H_2O$ | Comp. (%) | | |
| | | | | | | | | | MeOH | 2-PrOH | tBA |
| IX | KW-2000 | | | | FS-1 | 4.55 | 0.45 | 5.9 | 40.1 | 6.1 | 45.9 |
| | | 120 | 0.25 | 16 | 1 | 7.53 | 0.01 | 4.7 | 39.8 | 6.3 | 47.1 |
| | | | | 39 | 2 | 7.70 | 0.01 | 5.4 | 40.0 | 6.2 | 46.4 |
| | | | | 62 | 3 | 8.2 | 0.05 | 5.5 | 40.0 | 6.2 | 46.3 |
| | | | | 86 | 4 | 7.49 | 0.02 | 7.2 | 39.2 | 6.5 | 45.4 |

TABLE XII

| | | | | Time on Stream | tBA/MeOH Neutralization | | Acidity (mg | | Comp. (%) | | |
| --- | --- | --- | --- | --- | --- | --- | --- | --- | --- | --- | --- |
| Ex. | Base | Temp. (°C.) | LHSV | (Hrs) | Sample | pH | KOH/g) | $H_2O$ | MeOH | 2-PrOH | tBA |
| X | Magnesol | | | | FS-1 | 4.6 | 0.20 | 5.8 | 40.7 | 6.4 | 45.0 |
| | | 120 | 0.25 | 6 | 1 | 7.9 | 0.02 | 6.5 | 39.7 | 6.1 | 45.8 |
| | | | | 22 | 2 | 8.2 | 0.03 | 6.0 | 39.9 | 6.4 | 46.0 |
| | | | | 45 | 3 | 6.3 | 0.12 | 5.8 | 39.9 | 6.4 | 46.1 |
| | | | | 69 | 4 | 5.9 | 0.10 | 5.8 | 39.9 | 6.4 | 46.1 |
| | | | | 86 | 5 | 5.8 | 0.09 | 5.9 | 40.7 | 6.1 | 44.9 |

What is claimed is:

1. A method for removing organic acids and derivatives thereof from a crude methyl tertiary butyl ether (MTBE) stream of the type found in the feed to, or effluent from, a reactor for a one-step process for producing MTBE which comprises:

contacting said crude MTBE stream in a treating zone over one or more beds of a solid base selected from the group consisting of:

1) Hydrotalcites treated with an alkali metal selected from the group consisting of lithium, potassium, sodium, rubidium or cesium, and calcined prior to use;
2) Magnesium silicates generally derived from the interaction of a magnesium salt and a soluble silicate;
3) Amine functionalized polysiloxanes functionalized with ethylenediamine;
4) Zeolites exchanged with a metal selected from the group consisting of lithium, sodium, potassium, rubidium, cesium, calcium, barium, strontium and radium;
5) An oxide of Group III treated with a metal selected from lithium, potassium, sodium, rubidium and cesium; and
6) Weakly basic ion exchange resins, having a styrene-divinyl benzene polymer backbone and an amine functional structure selected from —$N(CH_3)_2$, —$NRH$ or —$NR_2$, where R is an alkyl group containing 2 to 20 carbon atoms, for a period of time sufficient to neutralize said organic acids and derivatives thereof; and withdrawing a substantially organic acid-free crude MTBE stream from said treating zone.

2. The method of claim 1 wherein the hydrotalcite is treated with sodium.

3. The method of claim 1 wherein the magnesium silicate is a synthetic, porous, high surface area amorphous magnesium silicate.

4. The method of claim 1 wherein the solid base catalyst is a Y-zeolite exchanged with a metal selected from sodium and cesium.

5. The method of claim 4 wherein the solid base is a sodium exchanged Y-zeolite further treated with cesium.

6. The method of claim 1 wherein the solid base catalyst is alumina modified with cesium.

7. The method of claim 6 wherein the alumina is further characterized as theta-alumina.

8. The method of claim 1 wherein the polymeric catalyst has the functional structure —$N(CH_3)_2$, an average pore diameter of 400 and an average surface area of 25 $m^2/g$.

9. The method of claim 1 further comprising adjusting the flow of crude MTBE to pass through the treating zone at a space velocity of 0.1 to 10 LHSV.

10. The method of claim 9 wherein the crude MTBE effluent is passed over the bed of solid base for a period of 10 to 1000 hours.

11. The method of claim 10 wherein the bed of solid base is maintained at a temperature between ambient and 150° C.

12. The method of claim 10 wherein the bed of solid base is operated at a pressure sufficient to maintain the effluent in liquid phase at operating temperatures.

* * * * *